(12) United States Patent
McLeod et al.

(10) Patent No.: US 6,419,686 B1
(45) Date of Patent: Jul. 16, 2002

(54) OCCLUSION DEVICE

(75) Inventors: Alan McLeod, Somerset; Peter Phillips, Abingdon, both of (GB)

(73) Assignee: Pearsalls Limited (GB)

( * ) Notice: Subject to any disclaimer, the term of this patent is extended or adjusted under 35 U.S.C. 154(b) by 0 days.

(21) Appl. No.: 09/463,766

(22) PCT Filed: Aug. 5, 1998

(86) PCT No.: PCT/GB98/02344

§ 371 (c)(1),
(2), (4) Date: Jan. 31, 2000

(87) PCT Pub. No.: WO99/07292

PCT Pub. Date: Feb. 18, 1999

(30) Foreign Application Priority Data

Aug. 5, 1997 (GB) .............................................. 9716497

(51) Int. Cl.[7] .............................................. A61M 29/00
(52) U.S. Cl. ...................................................... 606/200
(58) Field of Search .................................. 606/200, 191, 606/194, 198; 623/1.13, 1.15

(56) References Cited

U.S. PATENT DOCUMENTS 5,919,224 A * 7/1999 Thompson et al. ............ 623/1

FOREIGN PATENT DOCUMENTS

WO         WO-9641589 A1 * 12/1996 ............. A61F/2/06

* cited by examiner

*Primary Examiner*—Michael J. Milano
*Assistant Examiner*—Vy Q. Bui
(74) *Attorney, Agent, or Firm*—Craig A. Fieschko, Esq.; DeWitt Ross & Stevens S.C.

(57) ABSTRACT

An occlusion device comprising an occluding barrier, anchor means and means for retaining orientation. Preferred embodiments comprise means for urging the anchor means into position.

20 Claims, 4 Drawing Sheets

OCCLUSION DEVICE

This invention relates to surgical implants particularly, but not exclusively, for the occlusion of an iliac artery as part of the endovascular treatment of an abdominal aortic aneurysm.

The Ivancev-Malmö system of endovascular aneurysm exclusion is based on a tapered aortoiliac prosthesis in conjunction with a femorofemoral bypass and a contralateral common iliac artery occlusion. Many different forms of occlusion device have been in clinical use but they tend to be based on a closed-ended stentgraft, comprising a fabric bag and a cylindrical Gianturco Z stent. Devices have been used with the stent closed at both ends and also closed at only one end. However, the pelvic anatomy forces the common iliac artery into a tortuous path which makes it highly likely that the artery will be curved in two or three dimensions at the point where the occlusion device is deployed. The bending stiffness of the cylindrical stent used as the base of the occlusion device prevents both ends of the device forming a seal across the artery resulting in the leakage of arterial blood into the aneurysm.

The object of this invention is to provide an occlusion device that attempts to prevent the flow of blood in an artery irrespective of the curvature of the artery.

According to an aspect of the present invention there is provided an occlusion device comprising an occluding barrier, anchor means and means for retaining orientation of the barrier.

Preferably, the device includes means for urging the anchor means into position. This means may comprise, for example, a portion of the anchor means itself, a portion of the means for retaining orientation or a further component.

In preferred embodiments the anchor means and the orientation retaining means at least are configurably coupled. The main components can be made of a shape memory alloy or other suitable material such that they can adopt a collapsed condition for the purposes of placement and automatically expand thereafter. At least an upstream occluding barrier may form a concave face spanning the internal walls of the artery when the device adopts the expanded condition.

The occluding barrier diameter when the device is in the expanded condition is typically greater than 4 or 5 mm and can be much higher. The overall geometry of the device is preferably one in which the ratio of the length to the occluding barrier diameter is at least 2:1 but not more than about 10:1. A preferred ratio would be between about 3:1 to 8:1.

The sealing properties of the occluding barriers can be improved by providing them with a skirt of sealing elements of a material such as polyester known to encourage coagulation and light enough to be moved by leaking blood. Such skirts are most effective at downstream occluding barriers.

Preferred occlusion devices comprise a supporting structure having main components constructed from shape memory alloy (SMA) such as Nitinol which is a 50:50 alloy of titanium and nickel with a flexible occluding material such as a textile fabric or polymer sheet. The flexible occluding material may be used to form a complete surface covering of the supporting structure and/or to form at least one but preferably two barriers which are preferably held across the entire internal cross-sectional area of the artery by the supporting structure. The preferred location for the occluding barriers is at either end of the occlusion device where the barriers form end caps.

The preferred supporting structure can conform to the curvature of the artery in two ways: the central section may be recessed or absent to give room for the apex of the curved wall of the artery and/or the central section may be sufficiently flexible to allow the end caps of the occlusion device to be orientated by the artery wall such that both end caps are perpendicular to the long axis of the artery.

The flexible occluding component of the occlusion device may be of polyester or any suitably strong flexible and biocompatible material and may be formed using weaving, knitting, braiding or embroidery.

The attachment of the end caps to the supporting structure may be by any secure mechanical system such as suturing or by passing the wires of the supporting structure through the end caps.

The supporting structure and/or the flexible occluding material may be surface treated to improve their strength, fatigue resistance, biocompatibility or blood coagulation properties.

The preferred occlusion device is able to be inserted through a sheath and then preferably open out into its expanded state without the assistance of additional devices such as balloon catheters. This may be achieved using SMA by the heat setting of the supporting structure in its final state. Once cooled, the device can be compressed sufficiently to facilitate endovascular introduction preferably using a cooled introducing sheath. Once deployed, it is preferable that body temperature is sufficient to trigger a return to the memorised shape.

According to one embodiment of this invention, the occlusion device comprises a single braided supporting structure that has an hour-glass shape when expanded and end caps to prevent the flow of blood.

According to a second embodiment of this invention, the framework of the occlusion device comprises a pair of essentially cone-shaped supporting structures that have a flexible link joining them in the region of the apex of the cones.

According to a third embodiment of this invention, the framework of the occlusion device comprises a pair of cone-shaped supporting structures that are interconnected at the apex of the cones.

According to a fourth embodiment of this invention, the occlusion device comprises a pair of cylindrical stents linked by a flexible section of supporting material or linked just by a continuation of the textile sheath covering the stents.

According to another aspect of the present invention there is provided a skirt comprising sealing members light enough to be moved by leaking blood.

In this example, the skirt is provided around the sealing surface of the or each occluding barrier. The sealing members are moved so as to become tangled in the region of the sealing surface between the occluding barriers and the artery walls. Preferably, the sealing members comprise polyester or another suitable material with recognised coagulation enhancing properties.

In another aspect of this invention, an additional structure. in the form of a ring of multiple strands of a flexible material is attached to the edge of the downstream end cap of the occlusion device. The flexible strands may be individual strands of wire or textile or be narrow strips of textile fabric.

The strands preferably lie parallel to the device during insertion in order to minimise bulk. However, if blood should leak around the upstream end cap of the occlusion device, the flow of blood will tend to catch the free end of the flexible strands and push them towards the downstream end of the device. Any points of leakage around the downstream end cap will tend to be self-sealed by the effect of the flow of blood entangling the strands on the upstream side of the leak.

This aspect of the invention relates not only to occluding devices such as the subject of the first aspect of this invention but also to vascular prosthesis and stent devices.

According to another aspect of the present invention there is provided an occlusion device comprising first and second substantially cylindrical occluding barrier elements which are configurably coupled.

The invention, and its use, will now be described, by way of example, with reference to the accompanying drawings, in which.

Figure 1:
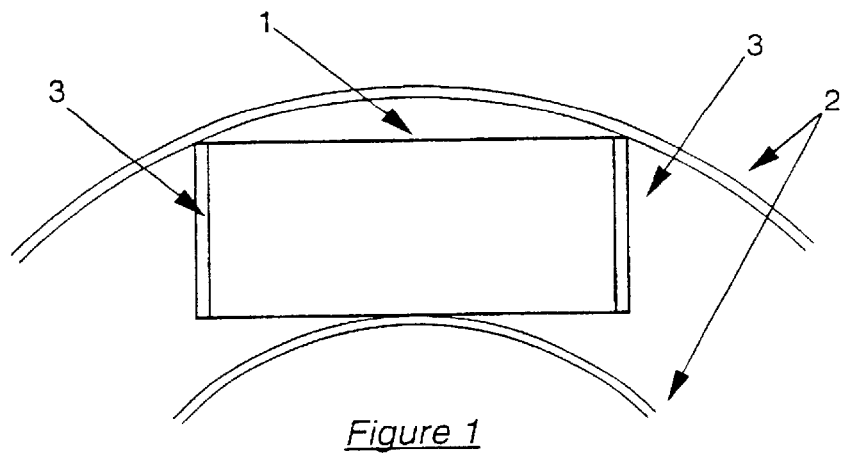
FIG. 1 is a view of a standard cylindrical occlusion device (1), of the type in current clinical use, seen in situ within a curved artery (2).

In FIG. 1, there is an illustration of the lack of conformity between the standard cylindrical occlusion device (1), of the type in current clinical use, and the internal anatomy of a curved artery (2). The end caps (3) are not perpendicular to the long axis of the artery (2), the curvature of which is holding the end caps (3) away from the artery wall resulting in unacceptable leakage.

Figure 2:
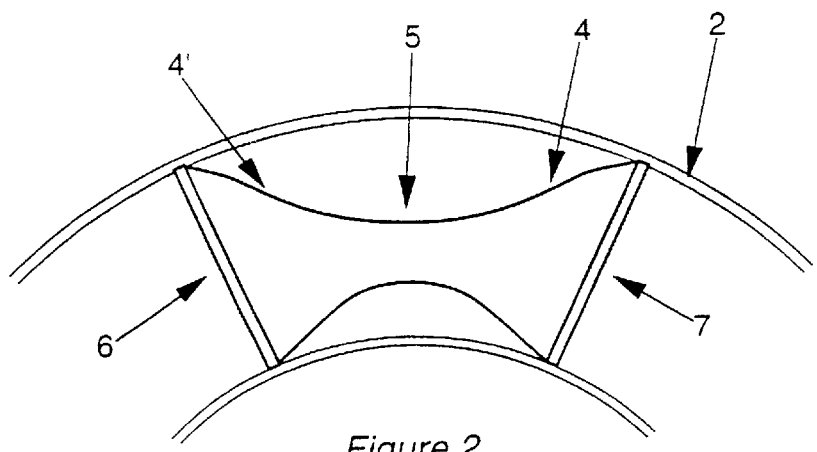
FIG. 2 is a view of an embodiment of this invention, seen in situ within a curved artery (2).

In FIG. 2, an embodiment of this invention is seen in situ within a curved artery (2). Occluding barriers are provided in the form of end caps (6, 7) one of which (6) is provided on an anchor means (4) and the other of which is provided on an orientation retaining means (4'). The means for retaining orientation (4') also functions as a means for intercepting impinging blood and transferring the force to the anchor means (4) to urge it into place within the artery. The waist of the occlusion device (5) prevents the end caps (6, 7) being pushed away from the wall of the artery while the flexible nature of the waisted section (5) allows the artery to automatically orientate the end caps (6, 7) such that they lie perpendicular to the long axis of the artery (2) and are in optimum contact with the artery wall.

Figure 3:
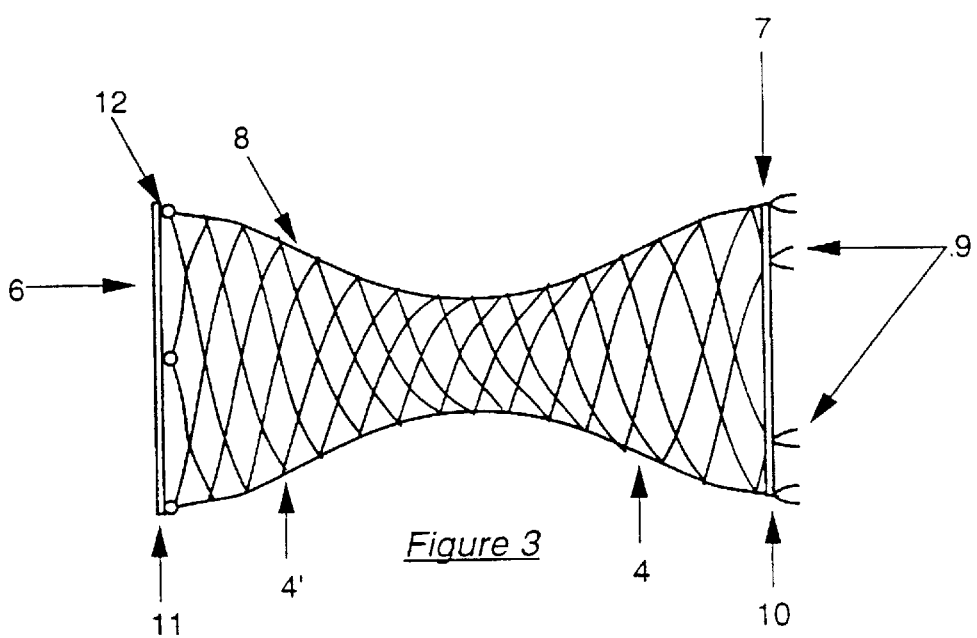
FIG. 3 is a view of a first embodiment of this invention comprising a single braided supporting structure in an hour-glass configuration (8), with textile end caps (6, 7) and retaining spikes (9) at the downstream end of the device (10).

In FIG. 3, a preferred embodiment of this invention is shown comprising a single braided supporting structure in an hour-glass configuration (8) formed of two conical portions (4, 4') with textile end caps (6, 7) and retaining spikes (9) at the downstream end of the device (10). The retaining spikes (9) are formed by a continuation of the wires forming the supporting structure (8) beyond the downstream end cap (7). These spikes are angled slightly outwards to engage the inner wall of the artery. The greater the blood pressure on the upstream end cap (6), the better the engagement of the spikes (9) into the artery wall although the depth of penetration of the spikes (9) is limited by the position of the end cap (7) itself. In this embodiment, there are no spikes at the upstream end of the occlusion device (11) and the braiding technique utilised provides closed loops of wire (12) rather than free ends. These loops (12) provide ideal location points for the secure mechanical attachment of the upstream end cap (6). Although the embodiment shown in FIG. 3 has two end caps (6, 7), the same supporting structure (8) could be used with either one end cap and/or a complete surface covering of flexible occlusion material in addition to the end caps. The occluding barrier at the upstream end of the device (end cap 6) provides a substantially concave barrier to blood flow.

Figure 4:
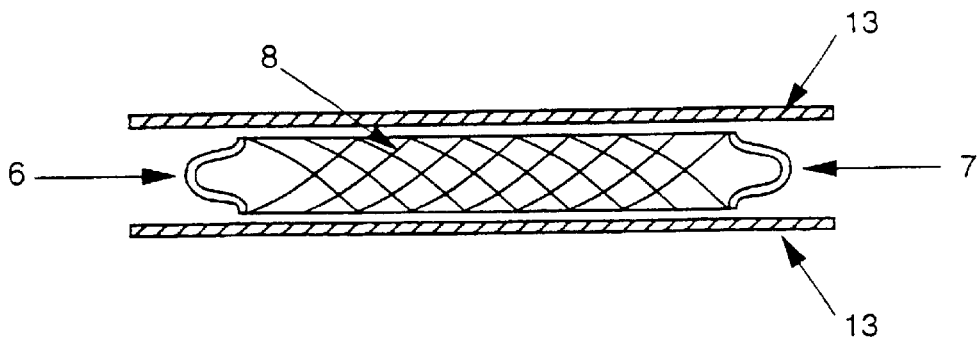
FIG. 4 is a view of the embodiment (8) shown in FIG. 3 in its insertion state.

In FIG. 4, the embodiment (8) shown in FIG. 3 can be seen in its insertion state. The braided supporting structure has been cooled and then crushed into a compact cylindrical shape. Before the crushing of the supporting structure, the centre of each end cap (6, 7) was pulled out beyond the supporting structure (8) in order to minimise the bulkiness of the device in the delivery sheath (13).

At least the upstream occluding barrier (i.e. end cap 6) should form a concave surface when the device is in place in the artery in its expanded state. Such concave surfaces stem and redirect the blood flow while minimising turbulence and other disruptive effects.

Figure 5:
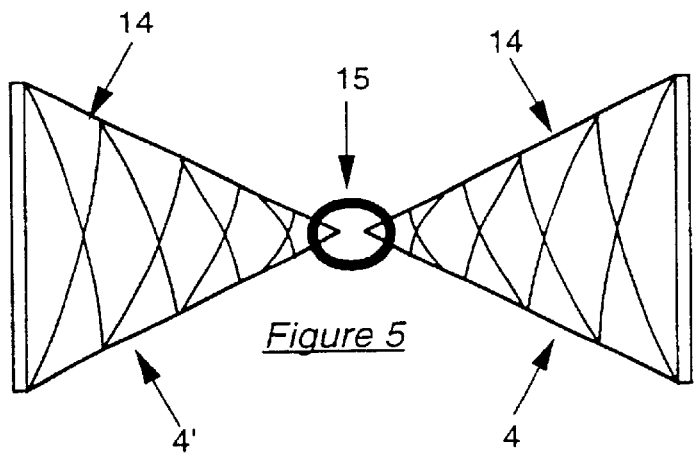
FIG. 5 is a view of a second embodiment of this invention comprising a pair of essentially cone-shaped supporting structures (14) with a flexible link at the apex of the cones (15).

In FIG. 5, a second embodiment of this invention is shown comprising a pair of essentially cone-shaped supporting structures (14) with a flexible link (15) at the apex of the cones. The supporting structure for the cones may be braided. The flexible link (15) may be a single wire loop such that the cones (14) are held with the apex of the cones pointing along the long axis of the artery but with sufficient flexibility that each cone can be orientated independently to ensure that the end caps produce the optimum seal across the artery.

Figure 6:
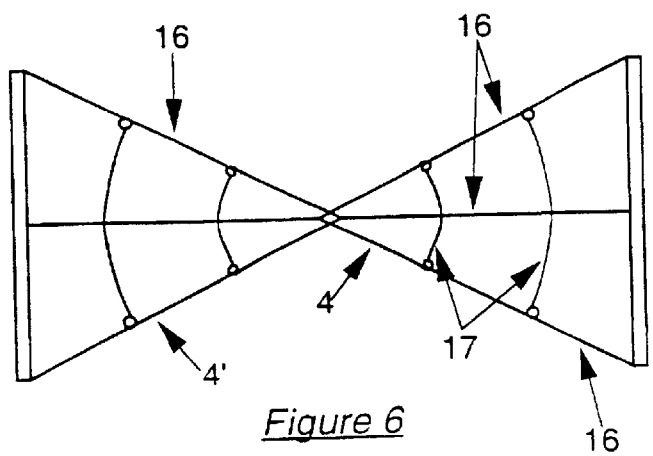
FIG. 6 is a view of a third embodiment of this invention with a pair of cone-shaped supporting structures that are interconnected at the apex of the cones.

In FIG. 6, a third embodiment of this invention is shown with a pair of coneshaped supporting structures that are interconnected at the apex of the cones. Each cone-shaped supporting structure is formed from a number of V-shaped struts (16) with circumferential supporting wires (17). The use of SMA wire for the V-struts ensures that the force acting on the internal wall of the artery is a constant irrespective of the diameter of the artery. Thus, the structure acts as an effective anchor to secure the device in place within the artery. This feature applies to all embodiments shown.

Figure 7:
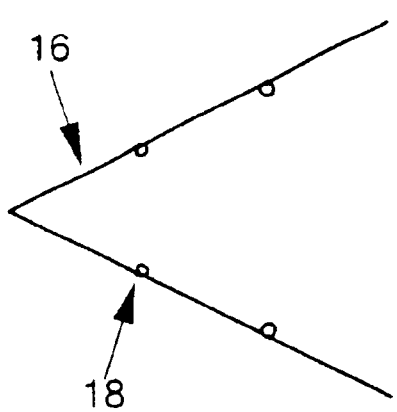
FIG. 7 is a plan view of one of the individual V-shaped wire struts (16) used in the construction of the embodiment shown in FIG. 6.

In FIG. 7, a plan view is shown of one of the individual V-shaped wire struts (16) used in the construction of the embodiment shown in FIG. 6. The strut (16). including the internal attachment loops (18), is formed from an individual SMA wire. The provision of the loops (18) facilitates the secure attachment of the circumferential supporting wires (17).

Figure 8:
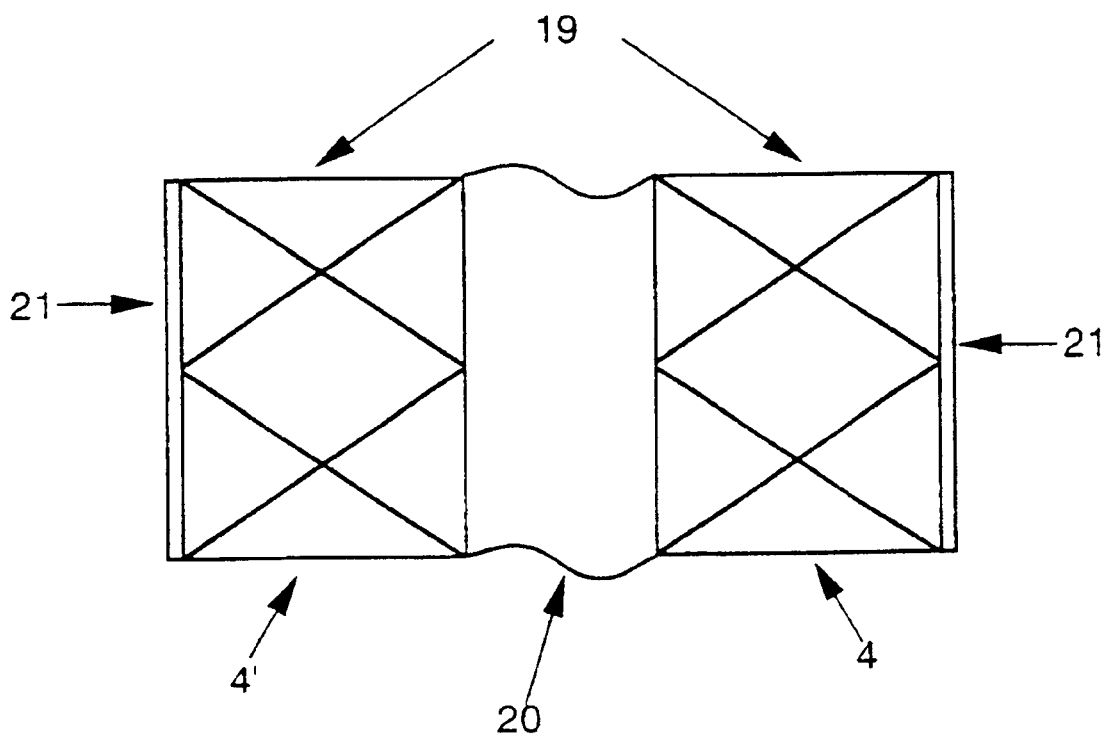
FIG. 8 is a view of a fourth embodiment of this invention with a pair of cylindrical stents (19) linked by a continuation of the textile sheath (20) covering the stents.

In FIG. 8, a fourth embodiment of this invention is shown with a pair of cylindrical stents (19) linked by a continuation of the textile sheath (20) covering the stents (19). This embodiment is most similar to the devices in current clinical use but the central gap in the supporting structure makes the device sufficiently flexible for the artery to orientate the individual stents (19) such that the end caps (21) are perpendicular to the long axis of the artery.

Figure 9:
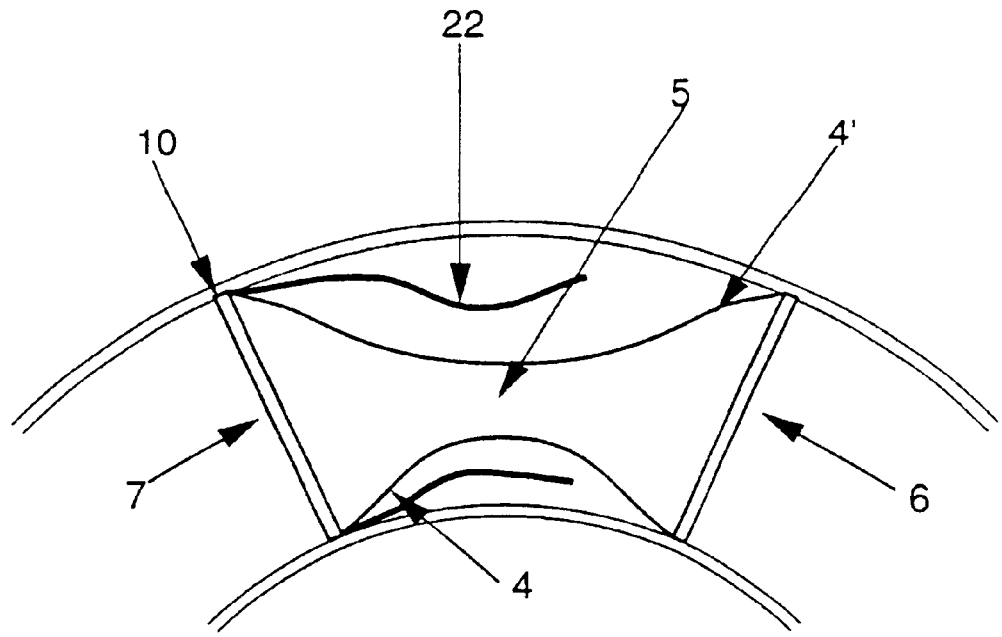
FIG. 9 is a view of the second aspect of the invention with the sealing strips (22) in the waisted section (5) of the occlusion device (8).

In FIG. 9, another aspect of this invention is illustrated. A skirt of sealing strips or wires or threads (22) is attached to the downstream edge of the occlusion device (10). During insertion and initial deployment, the sealing strips (22) are located in the waisted section (5) of the occlusion device with the maximum number of strands or strips to take advantage of the available space.

The sealing elements are light enough to be moved by leaking blood and end up tangled at the interface between the end cap 7 and the artery wall. This type of sealing device is most effective at downstream occluding barriers but may also be used at upstream occluding barriers.

Figure 10:
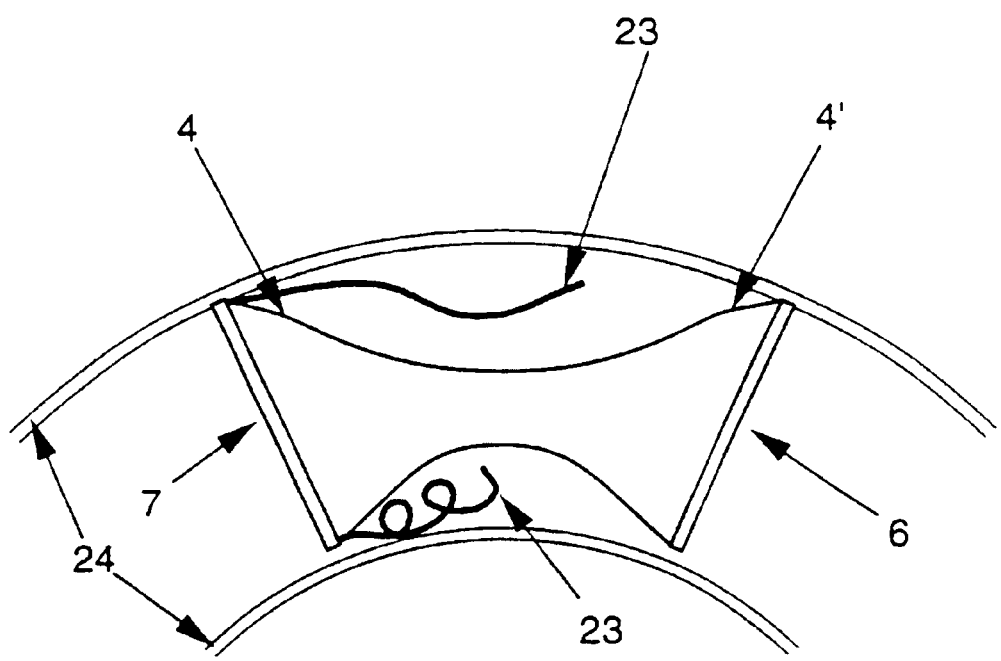
FIG. 10 is a view of the sealing strips (22) shown in FIG. 9 following a leak.

In FIG. 10, the effect is illustrated of a leak around the edge of both the upstream and downstream end caps (6, 7). The flow of blood past the waisted section of the occlusion device (5) has caught the free upstream end of the sealing strips (23) which have then been pushed in the direction of the leak around the edge of the downstream end cap (7). This automatically provides additional material precisely where it is required in order to eliminate the leak by plugging the gap between the end cap (7) and the artery wall (24).

In the embodiments described, the ratio of the overall length of the device to the diameter of the occluding barrier is between 2:1 and 10:1. This ratio need only be sufficient to prevent the device tumbling within the artery under the pressure of the blood flow. The ratio is preferably between about 3:1 and 8:1.

What is claimed is:

1. An arterial occlusion device comprising two opposing occluding barriers having a flexible central section interposed therebetween, whereby the central section may bend to allow the barriers to be oriented within nonparallel planes spaced apart within a curved section of artery, and wherein one or more flexible sealing elements extend from the occlusion device about or adjacent to at least one of the barriers, the sealing elements being collapsible to allow them to gather about the barrier when pushed by flow within the artery.

2. The arterial occlusion device of claim 1 wherein the circumference of the occlusion device increases between the central section and at least one of the barriers.

3. The arterial occlusion device of claim 2 wherein the arterial occlusion device has an hourglass shape between its barriers.

4. The arterial occlusion device of claim 1 wherein at least a portion of the occlusion device situated between the barriers is radially collapsible and expandible.

5. The arterial occlusion device of claim 1 wherein the occlusion device is radially collapsible and expandible adjacent its barriers.

6. The arterial occlusion device of claim 1 wherein at least a portion of the occlusion device located between the central section and one of the barriers is formed of a material having shape memory.

7. The arterial occlusion device of claim 6 wherein the portion of the occlusion device formed of shape memory material is radially collapsible.

8. The arterial occlusion device of claim 1 wherein a skirt of multiple sealing elements is provided about or adjacent to at least one of the barriers.

9. The arterial occlusion device of claim 1 wherein each sealing element is a flexible strand.

10. The arterial occlusion device of claim 1 wherein the ratio of the length of the device between its barriers to its diameter between its barriers is between about 2:1 to about 10:1.

11. The arterial occlusion device of claim 1 further comprising retaining spikes extending away from the central section at or adjacent to at least one of the barriers.

12. The arterial occlusion device of claim 1 wherein braided members extend between the barriers, the braided members allowing radial expansion and/or contraction of the device.

13. An arterial occlusion device comprising two opposing occluding barriers having a central section interposed therebetween, wherein the central section is recessed to have a lesser circumference than those of the barriers to thereby allow the apex of a curved artery wall to be received within the recess, and wherein the device includes one or more flexible sealing elements extending about or adjacent to at least one of the barriers, the sealing elements being foldable when subjected to flow within the artery.

14. The arterial occlusion device of claim 13 wherein the central section is flexible, whereby the central section may bend to allow the barriers to be oriented within nonparallel planes spaced apart within a curved section of artery.

15. The arterial occlusion device of claim 13 wherein at least a portion of the occlusion device situated between the barriers is radially collapsible and expandible.

16. The arterial occlusion device of claim 13 wherein the occlusion device, between its central section and at least one of its barriers, is at least partially formed of a material having shape memory.

17. The arterial occlusion device of claim 16 wherein the portion of the occlusion device formed of shape memory material is radially collapsible.

18. The arterial occlusion device of claim 13 wherein a skirt of multiple sealing elements is provided about or adjacent to at least one of the barriers.

19. The arterial occlusion device of claim 13 wherein each sealing element is a flexible strand.

20. The arterial occlusion device of claim 13 further comprising retaining spikes extending away from the central section at or adjacent to at least one of the barriers.

* * * * *